(12) United States Patent
Yamaguchi et al.

(10) Patent No.: US 7,186,821 B2
(45) Date of Patent: Mar. 6, 2007

(54) RICE SUCROSE TRANSPORTER GENE PROMOTER

(75) Inventors: Junji Yamaguchi, Aichi (JP); Chiaki Matsukura, Shizuoka (JP); Taito Takeda, Aichi (JP)

(73) Assignees: Japan Tobacco Inc., Tokyo (JP); Syngenta Limited, Surrey (GB)

( * ) Notice: Subject to any disclaimer, the term of this patent is extended or adjusted under 35 U.S.C. 154(b) by 0 days.

(21) Appl. No.: 10/250,763

(22) PCT Filed: Jan. 4, 2002

(86) PCT No.: PCT/JP02/00001

§ 371 (c)(1),
(2), (4) Date: Dec. 23, 2003

(87) PCT Pub. No.: WO02/055689

PCT Pub. Date: Jul. 18, 2002

(65) Prior Publication Data

US 2004/0253717 A1  Dec. 16, 2004

(30) Foreign Application Priority Data

Jan. 5, 2001 (JP) ............................. 2001-000651

(51) Int. Cl.
 *A01H 1/00* (2006.01)
 *C07H 21/04* (2006.01)
 *C12N 15/00* (2006.01)
(52) U.S. Cl. .................. 536/24.1; 435/6; 435/69.1; 435/410; 435/419; 435/320.1; 536/23.1; 800/278; 800/295
(58) Field of Classification Search ................ 800/295, 800/278; 435/320.1, 6, 69.1, 410, 419; 536/23.1, 536/24.1
See application file for complete search history.

(56) References Cited

U.S. PATENT DOCUMENTS 5,495,007 A    2/1996 Thompson et al.
6,613,960 B1 * 9/2003 Turgeon ..................... 800/278

FOREIGN PATENT DOCUMENTS

WO    WO99/09188    * 2/1999

OTHER PUBLICATIONS

Kim et al . Plant Mol Biol 1994. vol. 24, pp. 105-117.*
Truernit et al. Planta. 1995. vol. 196, pp. 564-570.*
XP002321129; Database Accession No. AF280050; P. R. Whitfeld; Oryza sativa sucrose transporter (SUT1) gene, Aug. 2, 2000.
Murakami et al., Shokubutsu Saibo Kogaku (Plant Cell Technology), 1992, vol. 4, No. 4 281-286 (with English Abstract).
Matsukura et al., Breeding Research 3, vol. 1, p. 23, 2001.
Ngampanya et al., Plant Cell Physiol., vol. 43, Supplement (2002) (abstract).
Riesmeier et al., The EMBO Journal, vol. 11, No. 13, 4705-4713, 1992.
Riesmeier et al., The Plant Cell, vol. 5, 1591-1598, Nov. 1993.
Gahrtz et al., The Plant Journal (1994) 6(5), 697-706.
Sauer et al., The Plant Journal (1994) 6(1), 67-77.
Truernit et al., Planta (1995) 196: 564-570.
Aoki et al., Plant Cell Physiol. 40(10): 1072-1078 (1999).
Matsukura et al., Plant Physiology, Sep. 2000, vol. 124, 85-93.
Ishiwatari et al., Planta (1998) 205: 12-22.
Altschul et al., Nucleic Acids Research, 1997, vol. 25, No. 17, 3389-3402.
Komari et al., The Plant Journal (1996) 10(1), 165-174.
Hiei et al., The Plant Journal (1994) 6(2), 271-282.
Kosugi et al., Plant Science, 70 (1990) 133-140.
Hirose et al., Plant Cell Physiol., vol. 38, No. 12, pp. 1389-1396 (1997).
Truernit et al., Planta, vol. 196, No. 3, pp. 564-570 (1995).

* cited by examiner

*Primary Examiner*—Phuong T. Bui
(74) *Attorney, Agent, or Firm*—Birch, Stewart, Kolasch & Birch, LLP

(57) ABSTRACT

The present invention provides DNA having the promoter activity of an OsSUT1 gene, as well as a transgenic plant and others capable of expressing a desired foreign gene specifically in the vascular bundle or the phloem thereof, using the above DNA as a promoter.

According to the present invention, DNA having the promoter activity of the OsSUT1 gene was isolated from the genomic library of rice (*Oryza sativa* L.) The DNA has a promoter sequence, which has a phloem specificity and a growing time specificity and exists in a nucleotide sequence shown in SEQ ID NO: 1. A transgenic plant expressing a foreign gene specifically in the phloem or in the vascular bundle system tissues was produced by ligating the desired foreign gene downstream of the promoter DNA and incorporating it into the genome of a plant.

14 Claims, 11 Drawing Sheets

(a)

Bar=0.2 mm
(b)

L: LARGE VASCULAR BUNDLE (LONGITUDINAL)
M: SMALL VASCULAR BUNDLE (LONGITUDINAL)
T: TRANSVERSE VASCULAR BUNDLE (c) Bar=0.02 mm

VB: LONGITUDINAL VASCULAR BUNDLE
TV: TRANSVERSE VASCULAR BUNDLE

LEAF BLADE (a)

Bar= 0.2 mm

ROOT (b)

Bar= 0.2 mm

CC: PHLOEM COMPANION CELL (c)

(d)

Bar= 0.1 mm

LEAF BLADE

Bar= 0.2 mm

ROOT (b)

Bar= 0.2 mm (c)

(d)

Bar= 0.1 mm

NODE (HEADING PERIOD) (a)

(b)

Bar= 0.1 mm

Bar= 1 mm

INTERNODE (HEADING PERIOD) (d)

Bar= 0.2 mm (c)

(e)

FLOWER (a) BEFORE FLOWERING (b)　　(c) AFTER FLOWERING

Bar= 2 mm (d)　Bar= 2 mm (e)　ANTHER, FILAMENT, PISTIL (P), LODICULE (L), GLUMOUS FLOWER

Bar= 0.012 mm

Figure 9

```
   1: TGCGCGGTAACCCACCATCAACCTCGCCGCGGCTTTAAATGCGCCGCTACAGGGCGCGTC    60
  61: CCATTCGCCATTCAGGCTGCGCAACTGTTGGGAAGGGCGATCGGTGCGGGCCTCTTCGCT   120
 121: ATTACGCCAGCTGGCGAAAGGGGGATGTGCTGCAAGGCGATTAAGTTGGGTAACGCCAGG   180
 181: GTTTTCCCAGTCACGACGTTGTAAAACGACGGCCAGTGAGCGCGCGTAATACGACTCACT   240
 241: ATAGGGCGAATTGGGTACCGGGCCCCCCCTCGAGGTCGACGGTATCGATAAGCTTGATAT   300
 301: CGAATTCGCTAGGCGTACACCGTGAATGATTTGATGCGTTGATTACGGGTATTCATATTC   360
 361: CTTTATGAAAGGTTATTGTCAGACTTTTTTTATTCCACAAGATCGATCATACTACAAAGT   420
 421: TATTCTACAATAGTTTAGAACACTTATCCAGTTGTGTTAGAATATAATAATGATGGATGG   480
 481: ATATGTATGCCATATTAAACAATCTAAATTCCCCACAAAACATATAAAAGAACACTATAA   540
 541: TAAACTATGGTTTATCCAACATGGACATATATTTAAATGAAGTGCGATCTCCGGTGCTCT   600
 601: TTACTGGTAGGATGAATGATGATAGAGATAAAAGCGTTTAACAAATATGGCCTCAAGCGA   660
 661: AATTCGTTATATTAATTAAATCAATGAAAACATTTACTGGATTAATAAAACTCCATGCTA   720
 721: CTCCATTATAAATGAACGCACACCTATATATAGCAAAATTCCTATTTGCCAGTAGGTCCA   780
 781: ATACTTCGGATCTGTTTTTTTTTCTTTTAAATATCCAAAATTGATTTTGGATAACTACTC   840
 841: GACAGTACAAACGAATTAAACCAGCTATTACAACGTCGAGTGGATTTAAAACACTCCTCT   900
 901: ATTAAATTCACCTACAGAAAGTCGTTCCCGCTGAAATAATCGCACCGTCTAGAAGCTCGG   960
 961: CAAGCGTGTCGCTAATCCGATACTAACTCCATTAATTCCATTTTCATTTCAATAATTGTT  1020
1021: GAAGTTATTACTGCACTGGAAATAATAAAGGCAGGGGGGTGTAACTGGGTGTGTACAAAG  1080
1081: TGTTGGTGAGCATAGCAGTTGGCAGGTGCACCACCCTTTATTATATTCCTCCTTTCTCTC  1140
1141: TCTCTCTCTCTCTCTCCCCCTCTTCCTCCCTTTAAATGCTTCGCCTCTCTCGCTCGTC   1200
1201: TCTCCAAACACAAACCCACCACCTCCTCCTCCTCCTCCCATCCAGCACGCGCCTCCTCTC  1260
1261: TCGCGCGGCTTTCCATTTCCATCTCCCCCTCCTCCTCCTACGTCTCCGCCGCTCCTCACT  1320
1321: TCCTCCACTCGATTTCCTTTCTTGGCCTCTCCTCCTCTGACACAGGGGTGTGCAGGTTTG  1380
1381: TGTTTGTGCGTGGCGCGTCCGCCATGGCTCGCGGCAGCGGGGCCGGAGGAGGCGGCGGCG  1440
```

※ UNDERLINE : *OsSUT1* promoter-1

ATG : TRANSLATION INITIATION SITE

Figure 10

```
   1: TGCGCGGTAACCCACCATCAACCTCGCCGCGGCTTTAAATGCGCCGCTACAGGGCGCGTC   60
  61: CCATTCGCCATTCAGGCTGCGCAACTGTTGGGAAGGGCGATCGGTGCGGGCCTCTTCGCT  120
 121: ATTACGCCAGCTGGCGAAAGGGGGATGTGCTGCAAGGCGATTAAGTTGGGTAACGCCAGG  180
 181: GTTTTCCCAGTCACGACGTTGTAAAACGACGGCCAGTGAGCGCGCGTAATACGACTCACT  240
 241: ATAGGGCGAATTGGGTACCGGGCCCCCCCTCGAGGTCGACGGTATCGATAAGCTTGATAT  300
 301: CGAATTCGCTAGGCGTACACCGTGAATGATTTGATGCGTTGATTACGGGTATTCATATTC  360
 361: CTTTATGAAAGGTTATTGTCAGACTTTTTTTATTCCACAAGATCGATCATACTACAAAGT  420
 421: TATTCTACAATAGTTTAGAACACTTATCCAGTTGTGTTAGAATATAATAATGATGGATGG  480
 481: ATATGTATGCCATATTAAACAATCTAAATTCCCCACAAAACATATAAAAGAACACTATAA  540
 541: TAAACTATGGTTTATCCAACATGGACATATATTTAAATGAAGTGCGATCTCCGGTGCTCT  600
 601: TTACTGGTAGGATGAATGATGATAGAGATAAAAGCGTTTAACAAATATGGCCTCAAGCGA  660
 661: AATTCGTTATATTAATTAAATCAATGAAAACATTTACTGGATTAATAAAACTCCATGCTA  720
 721: CTCCATTATAAATGAACGCACACCTATATATAGCAAAATTCCTATTTGCCAGTAGGTCCA  780
 781: ATACTTCGGATCTGTTTTTTTTTCTTTTAAATATCCAAAATTGATTTTGGATAACTACTC  840
 841: GACAGTACAAACGAATTAAACCAGCTATTACAACGTCGAGTGGATTTAAAACACTCCTCT  900
 901: ATTAAATTCACCTACAGAAAGTCGTTCCCGCTGAAATAATCGCACCGTCTAGAAGCTCGG  960
 961: CAAGCGTGTCGCTAATCCGATACTAACTCCATTAATTCCATTTTCATTTCAATAATTGTT 1020
1021: GAAGTTATTACTGCACTGGAAATAATAAAGGCAGGGGGGTGTAACTGGGTGTGTACAAAG 1080
1081: TGTTGGTGAGCATAGCAGTTGGCAGGTGCACCACCCTTTATTATATTCCTCCTTTCTCTC 1140
1141: TCTCTCTCTCTCTCTCTCCCCCTCTTCCTCCCTTTAAATGCTTCGCCTCTCTCGCTCGTC 1200
1201: TCTCCAAACACAAACCCACCACCTCCTCCTCCTCCTCCCATCCAGCACGCGCCTCCTCTC 1260
1261: TCGCGCGGCTTTCCATTTCCATCTCCCCCTCCTCCTCCTACGTCTCCGCCGCTCCTCACT 1320
1321: TCCTCCACTCGATTTCCTTTCTTGGCCTCTCCTCCTCTGACACAGGGGTGTGCAGGTTTG 1380
1381: TGTTTGTGCGTGGCGCGTCCGCC[ATG]GCTCGCGGCAGCGGGGCCGGAGGAGGCGGCGGCG 1440
```

※ UNDERLINE : OsSUT1 promoter-2

[ATG] : TRANSLATION INITIATION SITE

Figure 11

```
   1: TGCGCGGTAACCCACCATCAACCTCGCCGCGGCTTTAAATGCGCCGCTACAGGGCGCGTC   60
  61: CCATTCGCCATTCAGGCTGCGCAACTGTTGGGAAGGGCGATCGGTGCGGGCCTCTTCGCT  120
 121: ATTACGCCAGCTGGCGAAAGGGGGATGTGCTGCAAGGCGATTAAGTTGGGTAACGCCAGG  180
 181: GTTTTCCCAGTCACGACGTTGTAAAACGACGGCCAGTGAGCGCGCGTAATACGACTCACT  240
 241: ATAGGGCGAATTGGGTACCGGGCCCCCCCTCGAGGTCGACGGTATCGATAAGCTTGATAT  300
 301: CGAATTCGCTAGGCGTACACCGTGAATGATTTGATGCGTTGATTACGGGTATTCATATTC  360
 361: CTTTATGAAAGGTTATTGTCAGACTTTTTTTATTCCACAAGATCGATCATACTACAAAGT  420
 421: TATTCTACAATAGTTTAGAACACTTATCCAGTTGTGTTAGAATATAATAATGATGGATGG  480
 481: ATATGTATGCCATATTAAACAATCTAAATTCCCCACAAAACATATAAAAGAACACTATAA  540
 541: TAAACTATGGTTTATCCAACATGGACATATATTTAAATGAAGTGCGATCTCCGGTGCTCT  600
 601: TTACTGGTAGGATGAATGATGATAGAGATAAAAGCGTTTAACAAATATGGCCTCAAGCGA  660
 661: AATTCGTTATATTAATTAAATCAATGAAAACATTTACTGGATTAATAAAACTCCATGCTA  720
 721: CTCCATTATAAATGAACGCACACCTATATATAGCAAAATTCCTATTTGCCAGTAGGTCCA  780
 781: ATACTTCGGATCTGTTTTTTTTTCTTTTAAATATCCAAAATTGATTTTGGATAACTACTC  840
 841: GACAGTACAAACGAATTAAACCAGCTATTACAACGTCGAGTGGATTTAAAACACTCCTCT  900
 901: ATTAAATTCACCTACAGAAAGTCGTTCCCGCTGAAATAATCGCACCGTCTAGAAGCTCGG  960
 961: CAAGCGTGTCGCTAATCCGATACTAACTCCATTAATTCCATTTTCATTTCAATAATTGTT 1020
1021: GAAGTTATTACTGCACTGGAAATAATAAAGGCAGGGGGGTGTAACTGGGTGTGTACAAAG 1080
1081: TGTTGGTGAGCATAGCAGTTGGCAGGTGCACCACCCTTTATTATATTCCTCCTTTCTCTC 1140
1141: TCTCTCTCTCTCTCTCCCCCTCTTCCTCCCTTTAAATGCTTCGCCTCTCTCGCTCGTC   1200
1201: TCTCCAAACACAAACCCACCACCTCCTCCTCCTCCTCCCATCCAGCACGCGCCTCCTCTC 1260
1261: TCGCGCGGCTTTCCATTTCCATCTCCCCCTCCTCCTCCTACGTCTCCGCCGCTCCTCACT 1320
1321: TCCTCCACTCGATTTCCTTTCTTGGCCTCTCCTCCTCTGACACAGGGGTGTGCAGGTTTG 1380
1381: TGTTTGTGCGTGGCGCGTCCGCCATGGCTCGCGGCAGCGGGGCCGGAGGAGGCGGCGGCG 1440
```

※ UNDERLINE : *OsSUT1* promoter-3

ATG : TRANSLATION INITIATION SITE

SEQUENCE LISTING

<160> NUMBER OF SEQ ID NOS: 4

<210> SEQ ID NO 1
<211> LENGTH: 1440
<212> TYPE: DNA
<213> ORGANISM: Oryza sativa L.

<400> SEQUENCE: 1

```
tgcgcggtaa cccaccatca acctcgccgc ggctttaaat gcgccgctac agggcgcgtc      60
ccattcgcca ttcaggctgc gcaactgttg ggaagggcga tcggtgcggg cctcttcgct     120
attacgccag ctggcgaaag ggggatgtgc tgcaaggcga ttaagttggg taacgccagg     180
gttttcccag tcacgacgtt gtaaaacgac ggccagtgag cgcgcgtaat acgactcact     240
atagggcgaa ttgggtaccg ggccccccct cgaggtcgac ggtatcgata agcttgatat     300
cgaattcgct aggcgtacac cgtgaatgat ttgatgcgtt gattacgggt attcatattc     360
ctttatgaaa ggttattgtc agacttttt tattccacaa gatcgatcat actacaaagt     420
tattctacaa tagtttagaa cacttatcca gttgtgttag aatataataa tgatggatgg     480
```

-continued

```
atatgtatgc catattaaac aatctaaatt ccccacaaaa catataaaag aacactataa      540
taaactatgg tttatccaac atggacatat atttaaatga agtgcgatct ccggtgctct      600
ttactggtag gatgaatgat gatagagata aaagcgttta acaaatatgg cctcaagcga      660
aattcgttat attaattaaa tcaatgaaaa catttactgg attaataaaa ctccatgcta      720
ctccattata aatgaacgca cacctatata tagcaaaatt cctatttgcc agtaggtcca      780
atacttcgga tctgtttttt tttcttttaa atatccaaaa ttgattttgg ataactactc      840
gacagtacaa acgaattaaa ccagctatta caacgtcgag tggatttaaa acactcctct      900
attaaattca cctacagaaa gtcgttcccg ctgaaataat cgcaccgtct agaagctcgg      960
caagcgtgtc gctaatccga tactaactcc attaattcca ttttcatttc ataattgtt     1020 gaagttatta ctgcactgga aataataaag gcaggggggt gtaactgggt gtgtacaaag     1080
tgttggtgag catagcagtt ggcaggtgca ccacccttta ttatattcct cctttctctc     1140
tctctctctc tctctctccc cctcttcctc cctttaaatg cttcgcctct ctcgctcgtc     1200
tctccaaaca caaacccacc acctcctcct cctcctccca tccagcacgc gcctcctctc     1260
tcgcgcggct ttccatttcc atctccccct cctcctccta cgtctccgcc gctcctcact     1320
tcctccactc gatttccttt cttggcctct cctcctctga cacagggtg tgcaggtttg      1380 tgtttgtgcg tggcgcgtcc gccatggctc gcggcagcgg ggccggagga ggcggcggcg     1440
```

<210> SEQ ID NO 2
<211> LENGTH: 32
<212> TYPE: DNA
<213> ORGANISM: Artificial Sequence
<220> FEATURE:
<223> OTHER INFORMATION: Synthetic PCR forward primer

<400> SEQUENCE: 2
tcggcggccg cgatatcgaa ttcgctaggc gt         32

<210> SEQ ID NO 3
<211> LENGTH: 30
<212> TYPE: DNA
<213> ORGANISM: Artificial Sequence
<220> FEATURE:
<223> OTHER INFORMATION: Synthetic PCR primer

<400> SEQUENCE: 3
agctctagag ttggcaggtg caccaccctt         30

<210> SEQ ID NO 4
<211> LENGTH: 29
<212> TYPE: DNA
<213> ORGANISM: Artificial Sequence
<220> FEATURE:
<223> OTHER INFORMATION: Synthetic PCR reverse primer

<400> SEQUENCE: 4
ctgggatccg ccatggcgga cgcgccacg         29

RICE SUCROSE TRANSPORTER GENE PROMOTER

This application is the national phase under 35 U.S.C. § 371 of PCT International Application No. PCT/JP02/00001 which has an International filing date of Jan. 4, 2002, which designated the United States of America.

TECHNICAL FIELD

The present invention relates to a gene expression system targeting a plant, particularly targeting the vascular bundle system tissues of monocotyledons, and more particularly targeting the phloem in the vascular bundle. Specifically, the present invention relates to a DNA having a nucleotide sequence with the promoter activity of the rice sucrose transporter gene, an expression cassette, a transgenic plant transformed using these constructs.

PRIOR ART

Generally, the vascular system of plants has been well known as an organ for conducting assimilation products of photosynthesis or water. In addition, it has recently been reported that the vascular system is associated with signal transduction at an individual plant level, morphogenesis and the like. Sucrose transporter (hereinafter referred to as "SUT") is known as a protein that is mainly located in vascular bundle system tissues. SUT is a membrane protein which transports saccharose (sucrose) in higher plants, and it is considered that this protein plays a role in the active transport of sucrose, by coupling with $H^+$-ATPase localized in membranes, using the active transport of proton ($H^+$) as a driving force.

SUT gene has already been isolated from multiple plant species including dicotyledons. The plant from which SUT has been isolated for the first time is spinach (Riesmeier J W, Willmitzer L, Frommer W B (1992), Isolation and characterization of a sucrose carrier cDNA from spinach by functional expression in yeast. EMBO J 11: 4705–4713).

It has been confirmed that SUT isolated from a dicotyledon, Solanum tuberosum, is expressed specifically in the phloem in the vascular bundle (Riesmeier J W, Hirner B, Frommer W B (1993), Potato sucrose transporter expression in minor veins indicates a role in phloem loading. Plant Cell 5: 1591–1598). Subsequently, the expression of SUT specific to the phloem in the vascular bundle has been reported for other plants including Plantago (Gahrtz M, Stolz J, Sauer N (1994), A phloem-specific sucrose-$H^+$ symporter from Plantago major L. supports the model of apoplastic phloem loading. Plant J. 6: 697–706) and Arabidopsis thaliana (Sauer N, Stolz, J (1994) SUC1 and SUC2: two sucrose transporters from Arabidopsis thaliana; expression and characterization in baker's yeast and identification of the histidine-tagged protein. Plant J 6: 67–77). Moreover, the expression of the SUC specific to the phloem in vascular bundle has also been confirmed in other plants such as Arabidopsis, tomato and garden pea.

The promoter of the above dicotyledon, Arabidopsis, has already been isolated, and the analysis of the expression system has been carried out using a "promoter: GUS system" and a "promoter: GFP transformant" system (Truernit E, Sauer N (1995), The promoter of the Arabidopsis thaliana SUC2 sucrose-$H^+$ symporter gene directs expression of β-glucuronidase to the phloem: Evidence for phloem loading and unloading by SUC2. Planta 196: 564–570: Imalau A., Truernit E., Sauer N. (1999), Cell-to-cell and long-distance trafficking of the green fluorescent protein in the phloem and symplastic unloading of the protein into sink tissues. Plant Cell 11: 309–322).

In the case of monocotyledons, SUT gene was first isolated from rice (Hirose T, Imaizumi N, Scofield G N, Furbank R T, Ohsugi R (1997), cDNA cloning and tissue specific expression of a gene for sucrose transporter from rice (Oryza sativa L.), Plant Cell Physiol 38: 1389 to 1396). Thereafter, SUT gene has also been isolated from maize and other plants (Aoki N., Hirose T., Takahashi S., Ono K., Ishimaru K., Ohsugi R. (1999), Molecular cloning and expression analysis of a gene for a sucrose transporter in maize (Zea mays L.). Plant Cell Physiol. 40: 1072–1078).

Rice is the only monocotyledon in which SUT gene expression has been confirmed to be localized in the phloem (Matsukura C. et al., 2000, Plant Physiol. 124: 85–94). Moreover, although it is not a report regarding SUT, a RPP13-1 gene with the promoter thereof has been isolated as a gene which is expressed specifically in the phloem (Ishiwatari Y, Fujiwara T, McFarland K C, Nemoto K, Hayashi H, Chino M, Lucas W J (1998), Rice phloem thioredoxin h has the capacity to mediate its own cell-to-cell transport through plasmodesmata. Planta 205: 12–22).

In addition, there have been some reports regarding promoters that control gene expression specific to the phloem (U.S. Pat. No. 5,495,007, DE Pat. No. 4,306,832, International Publications WO93/04177, WO92/22582, WO91/09050 and WO00/11197), but none of these reports relate to SUT gene promoter.

SUMMARY OF THE INVENTION

In recent years, in the development of genetic transformation technology for plants, gene expression systems which use a promoter specific to a tissue, an organ or a growth stage, has been required in place of conventional systemic or constant gene expression systems. In particular, the establishment of an expression system of a useful gene that targets vascular bundle system tissues, acting also as an infection route of pathogenic fungi or viruses, can be expected to be an important means for imparting disease resistance, converting the transport capacity of vascular bundle by genetic transformation, improving herbaceous type by genetic transformation, and others.

Most of all, the specific expression system, targeting vascular bundles, of a gene of interest such as an insecticidal protein, antiviral protein or disease resistance protein will be extremely useful in rice that is an important crop. In addition, the specific expression in vascular bundles of proteins participating in the sugar metabolism (sucrose synthase, sucrose phosphate synthase, etc.) or sugar transport (SUT, $H^+$-ATPase, etc.) system or a gene encoding a sugar signal transduction factor, which is directed towards the improvement of sugar transport through vascular bundles, and further, the specific expression of a certain protein to promote transportation of substances through the phloem, are also desired.

Thus, it is industrially very important to construct a gene expression system which is capable of expressing a desired gene in a manner targeting at vascular bundle system tissues of a higher plant, rice, by exploiting the controlling function of a promoter.

However, no SUT gene promoter of monocotyledons has previously been isolated, and there are only a few reports of promoters which control gene expression specific to the phloem in the vascular bundle of monocotyledons.

It is an object of the present invention to isolate a promoter from major monocotyledon crops, particularly from the rice plant, which is specific for the vascular bundle tissues, and more particularly for the phloem thereof. It is another object of the present invention to provide a transgenic plant with the above described various improvements by applying the controlling function of SUT gene promoter. The present invention further provides a method of producing the above transgenic plant, and an expression vector as well as an expression cassette, which can be used in the method.

BRIEF DESCRIPTION OF THE DRAWINGS

FIG. 2a schematically shows the running state of vascular bundles on a rice leaf, FIG. 2b is magnified picture of tissues corresponding to a portion of the rice leaf of FIG. 2a, and FIG. 2c is a magnified picture of a transverse vascular bundle of a leaf in a cross sectional view.

FIG. 3a is a magnified picture of the surface of a leaf, FIG. 3b is a magnified picture of a root, FIG. 3c is a set of magnified pictures showing a leaf in cross sectional view, and FIG. 3d is a set of magnified pictures showing a root in cross sectional view. In the figures, L, M, T and cc represent a large vascular bundle (longitudinal), a small vascular bundle (longitudinal), a transverse vascular bundle and a phloem companion cell, respectively.

FIG. 4a is a magnified pictures of the surface of a leaf, FIG. 4b is a magnified pictures of a root, FIG. 4c is a set of magnified pictures showing a leaf in cross sectional view, and FIG. 4d is a set of magnified pictures showing a root in cross sectional view. In the figures, L, M and T represent a large vascular bundle (longitudinal), a small vascular bundle (longitudinal) and a transverse vascular bundle, respectively.

FIG. 5a is a set of magnified pictures showing the surface of a leaf. The upper panel shows an individual plant in which GUS is expressed but the expression is not specific to vascular bundles, and the lower panel shows an individual in which GUS is not expressed. FIG. 5b is a cross sectional magnified picture of the leaf, of the upper panel of FIG. 5a. FIG. 5c is a set of magnified pictures of a root in cross sectional view. In the figures, L, M and T represent a large vascular bundle (longitudinal), a small vascular bundle (longitudinal) and a transverse vascular bundle, respectively.

FIG. 6a is a cross sectional photographic view of a node during the heading period. Each of FIGS. 6b and 6c is a magnified picture of a portion of the node of FIG. 6a. FIG. 6d is a set of magnified picture of the surface of an internode during the heading period, in which the left panel shows a differentiation zone, the center panel shows an elongation zone, and the right panel shows a maturation zone. FIG. 6e schematically shows the positions of the differentiation zone, the elongation zone and the maturation zone in an internode. In the figure, VB is a vascular bundle, P is phloem, and X is xylem.

FIG. 7e schematically shows the structure of a flower organ. In the figures, L represents a lodicule and P represents a pistil.

FIG. 8a shows a stigma before flowering, FIG. 8b shows an ovary at 3 days after flowering, and FIG. 8c shows a pericarp vascular bundle at 10 days after flowering. FIG. 8d shows a longitudinal segment of a stigma before flowering, FIG. 8e shows a transverse segment of an ovary wall at 3 days after flowering, and FIG. 8f shows a transverse segment of the phloem in a pericarp vascular bundle at 10 days after flowering.

FIG. 9 shows the position of OsSUT1-promoter-1 which is underlined in the nucleotide sequence corresponding to SEQ ID NO: 1.

FIG. 10 shows the position of OsSUT1-promoter-2 which is underlined in the nucleotide sequence corresponding to SEQ ID NO: 1.

FIG. 11 shows the position of OsSUT1-promoter-3 which is underlined in the nucleotide sequence corresponding to SEQ ID NO: 1.

DETAILED DESCRIPTION OF THE INVENTION

Figure 1:
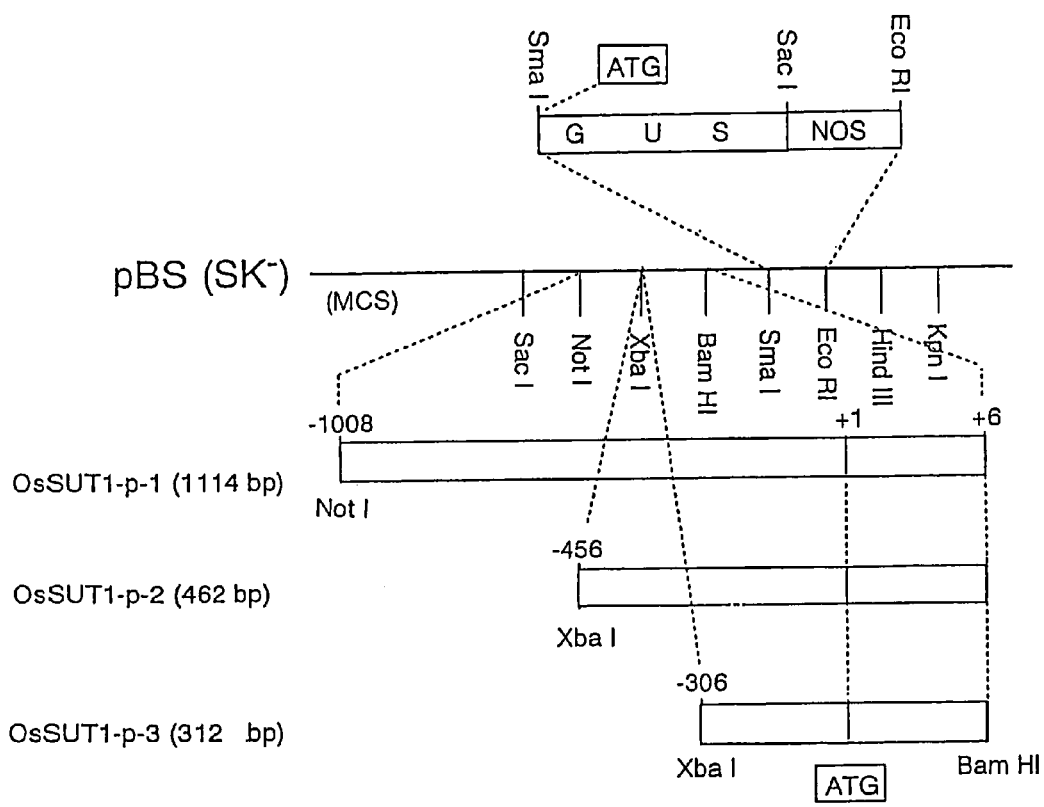
FIG. 1 shows the construction of a GUS expression vector comprising OsSUT1 promoter.

As a result of intensive studies, the present inventors have identified DNA having the promoter activity of OsSUT1 gene from the genomic library of a rice plant (*Oryza sativa* L.; variety: Aoinokaze) for the first time, and have determined its nucleotide sequence. They have found that this promoter is capable of expressing a structural gene ligated downstream thereof specifically in the phloem in the vascular bundle of a plant or in the vascular bundle during the flowering period. They produced an expression cassette comprising a foreign structural gene ligated in the downstream of the promoter, and also produced a vector comprising the expression cassette. They then succeeded in actually producing a transgenic plant, which was transformed using the vector, thereby accomplishing the present invention.

Moreover, the present inventors also have found that when a portion of the 5'-side of the above nucleotide sequence is deleted, the phloem specificity is lost and the gene is expressed in the entire vascular bundle system tissues, and that the expression specificity in respect of growth stage is also altered. These findings mean that the OsSUT1 gene promoter exhibits different features between the 5'-side and the 3'-side regions, suggesting that by use of the different features, an expression system which enables controlling of an expression site and a growth stage can be constructed.

Promoter

That is to say, the present invention provides a DNA which contains a promoter sequence existing in the nucleotide sequence of SEQ ID NO: 1. The term "promoter" is generally used in the present specification to mean a nucleotide sequence existing upstream of the transcription initiation point of a structural gene and controlling the expression of the gene. Thus, the term promoter also includes e.g., transcription controlling sequences such as an enhancer.

OsSUT1-promoter-1

More specifically, the first promoter existing in the nucleotide sequence shown in SEQ ID NO: 1, named "OsSUT1-promoter-1", is a DNA, which comprises a nucleotide sequence ranging from a nucleotide in the region from nucleotide "285 (T) through nucleotide 296 (G)" to a nucleotide in the region from nucleotide "1088 (G) through nucleotide 1403 (C)" in the nucleotide sequence shown in SEQ ID NO: 1, or a nucleotide sequence where a portion of the region from the 5'-end through nucleotide 947 (G) is deleted in the above nucleotide sequence; and has a strong site-specific promoter activity directed to the phloem site in the vascular bundle of plants. In addition to the promoter activity specific to the phloem in the vascular bundle in green leaves and roots, this promoter also has an activity specific to the phloem in the vascular bundle and to growth stage, in nodes, internodes and flower organs during the ear emergence and flowering periods.

The present invention further provides a DNA which hybridizes with the OsSUT1-promoter-1 under highly stringent conditions and has a substantially identical promoter activity, especially the promoter activity specific to the phloem in the vascular bundle tissues.

The present invention further provides a DNA, which comprises a nucleotide sequence having insertion, addition, deletion or substitution of one or more nucleotides in the nucleotide sequence of the OsSUT1-promoter-1, and has a substantially identical promoter activity, especially the promoter activity specific to the phloem in the vascular bundle tissues.

The present invention further provides a DNA, which is highly homologous with the nucleotide sequence of the OsSUT1-promoter-1, and has a promoter activity substantially identical to the OsSUT1-promoter-1, especially the promoter activity specific to the phloem in the vascular bundle tissues. The nucleotide sequence of the DNA shows at least 80%, preferably 85% or more, and more preferably 95% or more homology with that of the OsSUT1-promoter-1. The level of homology (%) can be determined using, for example, the BLAST program described in Altschul et al., Nucl. Acids. Res. 25., pp. 3389–3402 (1997). The BLAST program can easily be obtained through the internet.

OsSUT1-Promoter-2

The second promoter existing in the nucleotide sequence shown in SEQ ID NO: 1, named "OsSUT1-promoter-2", is a DNA, which comprises a nucleotide sequence from "T at nucleotide 948 through C at nucleotide 1403" in the nucleotide sequence shown in SEQ ID NO: 1 and has a promoter activity specific to the vascular bundle tissues of plants. This promoter has a low phloem-specificity, but maintains the specificity to the vascular bundle tissues of plants. For example, this promoter has activity specific to the phloem, xylem and parenchymatous cells in the vascular bundles of green leaves and roots. Moreover, the vascular bundle system tissue-specific activity of this promoter tends to less dependent on growing period and organ when compared with that of the above first promoter.

The present invention further provides a DNA which hybridizes with the OsSUT1-promoter-2 under highly stringent conditions and has a substantially identical promoter activity, especially the promoter activity specific to the plant vascular bundle tissues.

The present invention further provides a DNA, which comprises a nucleotide sequence comprising insertion, addition, deletion or substitution of one or more nucleotides in the nucleotide sequence of the OsSUT1-promoter-2, and has a substantially identical promoter activity, especially the promoter activity specific to the plant vascular bundle tissues.

The present invention further provides a DNA, which is highly homologous with the nucleotide sequence of the OsSUT1-promoter-2, and has a promoter activity substantially identical to the OsSUT1-promoter-2, especially the promoter activity specific to the plant vascular bundle tissues. The nucleotide sequence of the DNA shows at least 80%, preferably 85% or more, and more preferably 95% or more homology with that of the OsSUT1-promoter-2. The level of homology (%) can be determined using, for example, the BLAST program described in Altschul et al., Nucl. Acids. Res. 25., pp. 3389 to 3402 (1997). The BLAST program can easily be obtained through the internet.

It should be noted that TATTATA from nucleotides 1119 to 1125 of SEQ ID NO: 1 is assumed to be TATA box. Accordingly, in a preferred embodiment of the present invention, OsSUT1-promoter-1 and OsSUT1-promoter-2 extend such that the 3'-end reches A at nucleotide 1125 or a nearby nucleotide thereto in SEQ ID NO: 1.

Preparation of Promoter

Isolation, purification and cloning of OsSUT1 promoter, the construction of the expression vector, the transformation and regeneration of the plant cells, and others of the present invention can be carried out by those skilled in the art by referring to the examples disclosed in the specification, or by techniques known in the field of genetic engineering. Those skilled in the art can easily understand detailed experimental methods, when they refer to documents cited in the present specification or other appropriate documents.

For example, the DNA having the OsSUT1 promoter activity of the present invention can be obtained as follows. Using, as a probe, the entire or a part of appropriate promoter activity portion of the nucleotide sequence shown in SEQ ID NO: 1, a genomic DNA library of a monocotyledon, preferably a rice plant (*Oryza sativa* L.), may be screened by a method such as colony hybridization. A DNA of interest may be selected from among colonies comprising a DNA fragment, e.g. with a length of approximately 1,000 bp, and hybridizing with the probe.

Conditions for the hybridization should be "highly stringent." That is to say, hybridization conditions with a hybridization buffer (0.5 M $Na_2HPO_4$, 7% SDS, 1% polyvinylpyrrolidone) and a temperature of approximately 63° C. or higher, preferably approximately 65° C. or higher are prefered. By repeating the screening twice or more, and preferably three times or more under such hybridization conditions, it is possible to obtain a DNA, which has a nucleotide sequence identical to, or highly homologous with, for example, approximately 85% or more, and preferably approximately 95% or more homologous with the nucleotide sequence of the above OsSUT1-promoter-1 or -2: and has a substantially identical promoter activity.

Moreover, a DNA comprising "a nucleotide sequence comprising an insertion, addition, deletion or substitution of one or several nucleotides" with respect to the nucleotide sequence of the above OsSUT1-promoter-1 or -2, can easily be obtained from the OsSUT1-promoter-1 or -2, or from a DNA homologous therewith, by e.g., site-directed mutagenesis. Such mutagenesis can be carried out not only by the above site-directed mutagenesis, but also by any method known to a person skilled in the art.

The obtained DNA fragment is amplified by a known technique, PCR, and its nucleotide sequence is determined. Subsequently, by comparing the determined sequence with the nucleotide sequence of SEQ ID NO: 1, it can be confirmed that it is a promoter of interest.

In order to directly confirm the promoter activity of the DNA fragment, a reporter gene is ligated downstream of the 3'-side of the DNA so as to produce an expression vector, and the obtained expression vector is then introduced into a plant cell. Examples of reporter genes, the expression of which in a transgenic plant is detected, include GUS, LacZ and Cat genes, as their expression can be easily assayed and quantitated; and reporter genes also include those which can be tested of the tissue specificity in the expression such as above GUS gene, GFP gene and other genes. An established known assay can be used for each reporter gene. When the expression specificity of the DNA fragment is confirmed by examining the promoter activity, the sequence of the DNA fragment can be selected as a "nucleotide sequence of the expected region having a promoter activity" for the following selection of desired expression specificity.

Expression Cassette and Vector

The DNA having the promoter activity according to the present invention can be used as an expression cassette together with a foreign gene, which is to be expressed in a manner specific to phloem in a vascular bundle, the vascular bundle, or an organ, or a growth stage.

Any gene other than OsSUT1 gene can be used as a "foreign gene", as long as it can be expressed in the above vascular bundle, especially in the phloem in the vascular bundle under the control of the DNA having the promoter activity of the present invention. A typical example includes a gene encoding a protein, which has a useful action when the gene is expressed specifically in the area of the vascular bundle. Focusing attention on the fact that a vascular bundle acts as an infection route, examples of a preferred foreign gene include proteins which impart disease resistance to plant bodies. Among them, an anti-pest protein, antibacterial protein or antiviral protein is especially useful. Paying attention to the fact that the formation of a vascular bundle system plays an important role in the morphogenesis of an individual plant, it is also possible to express a gene controlling herbaceous height or herbaceous type, targeting the entire vascular bundle. Examples of particularly preferred genes include GAI gene associated with the signal transduction of gibberellin, and the like.

A method of constructing an expression cassette by ligating a foreign gene of interest to the 3'-side of a promoter region is known to a person skilled in the art. The constructed cassette is then amplified in an appropriate vector (e.g., pBSII, or other vectors belonging to the same type). The amplified expression cassette can be incorporated in the genome of a plant cell by homologous recombination, for example, by way of an intermediate vector for recombination. The constructed cassette is introduced into *Escherichia coli* or the like for amplification. Moreover, the cassette can be introduced into *Agrobacterium* by triple cross, using *Agrobacterium* and two types of *Escherichia coli* (one of which is *Escherichia coli* containing the cassette).

The above described expression cassette may comprise, as appropriate, an enhancer sequence, untranslated regions at the 5'- and 3'-sides of a foreign gene, and others. Moreover, the expression cassette may further comprise a marker gene to select a transformant. Examples of marker genes include resistance genes for antibiotics such as tetracycline, ampicillin, kanamycin, neomycin, hygromycin or spectinomycin; luciferase gene; β-galactosidase gene; β-glucuronidase (GUS) gene; green fluorescence protein (GFP) gene; β-lactamase gene; chloramphenicol acetyltransferase (CAT) gene; and others.

Introduction of Expression Cassette into Plant Cell

The present invention also provides a transgenic plant in which the above described expression cassette is incorporated into the genome of said plant transformed with the above described expression vector, whereby the promoter activity allows a foreign gene to be expressed specifically in the vascular bundle tissues, especially in the phloem thereof.

A method of introducing a foreign gene into a plant cell genome using the above described expression cassette is not particularly limited, and examples of the method include *Agrobacterium* method, electroporation, PEG method, microinjection, particle gun method and others. A preferred method is the *Agrobacterium* method. The details of the *Agrobacterium* method are described in e.g., PCT International Publication WO92/13957. As will be described in examples later, this method involves the application of the native transformation ability of *Agrobacterium*. The method preferably comprises transferring an expression cassette into *Agrobacterium* by conjugation or the like from an intermediate vector containing the expression cassette, and then infecting a plant with this *Agrobacterium*. The method of infecting a plant with *Agrobacterium* is well known to a person skilled in the art, and examples of the method include a method of partly damaging plant tissue and infecting the plant with bacteria therefrom, a method of infecting the embryonic tissues (including immature germ cells) of a plant with bacteria, a method of infecting a plant callus with bacteria, a method of coculturing protoplasts and bacteria, and a method of culturing a segment of leaf tissues with bacteria (leaf disk method).

The obtained transformed cell can be selected from among other cells by using an appropriate marker as an index, or by determining whether or not it expresses a desired character. A method of culturing the transformed plant cell in a regeneration medium to obtain a complete plant is described in e.g., Y. Hiei et al., Plant J. 6. 271–282: 1994.

The analysis of the obtained transformed plant can be carried out by various methods well known to a person skilled in the art. For example, oligonucleotide primers are synthesized on the basis of the DNA sequence of the introduced gene, and then PCR is carried out using these primers to analyze the chromosomal DNA of the transgenic plant. Moreover, the analysis can also be carried out by checking the presence or absence of mRNA or protein expression corresponding to the introduced gene. Furthermore, the analysis can also be carried out from the appearance of the plant (for example, where a gene encoding a protein capable of generating local necrotic spots is introduced, the presence or absence of the local necrotic spots, or the size or number of the spots, etc., can be checked), disease resistance (for example, the presence or absence of resistance or the resistance level when the plant is contacted with pathogenic fungi), and others.

By way of an example, a foreign gene can be introduced into the genome of a plant cell together with the promoter of the present invention by the following steps:

(a) providing a promoter of the present invention;
(b) ligating a desired structural gene downstream of the above promoter, and, if necessary, further ligating a selection marker gene after the above structural gene so as to produce an expression cassette;

(c) introducing the above expression cassette into the genome of a plant by the *Agrobacterium* method, electroporation, PEG method, microinjection or particle gun method;

(d) screening transformed plant cells by the selection marker and culturing the obtained cells to form a callus;

(e) culturing the generated callus in a regeneration medium until it becomes a complete plant; and (d) as desired, breeding the obtained plant by self-pollination or cross-pollination, and thereby establishing a variety of homozygous transgenic plants.

It should be noted that the term "transformant" is used in the present specification to include not only transformants which are obtained by the method of the present invention comprising obtaining recombinant plant cells and then regenerating a plant from the plant cells, but also progeny plants obtained from the transformants, as long as their expression specificity is maintained. The term "plant" is used herein to include, unless otherwise specified, not only a plant (individual), but also seeds (including germinated seeds and immature seeds), organs or portions thereof (including leaf, root, stem, flower, stamen, pistil and segments thereof), plant culture cells, calluses, and protoplasts.

ADVANTAGES OF THE INVENTION

The present invention provides a DNA having a promoter activity extremely useful for higher plants and an expression cassette containing the DNA, and a novel gene expression system, which has not been accomplished with the conventional vascular bundle expression system, are thereby provided.

In particular, the use of OsSUT1-promoter-1 as a promoter enables a gene of interest to be expressed specifically in the phloem in the vascular bundle of rice plants. Moreover, OsSUT1-promoter-1 is useful also as a gene expression promoter targeting the phloem companion cells in the vascular bundle during the reproductive period (reproductive organs, nodes and internodes during the ear emergence and flowering periods).

Furthermore, the use of OsSUT1-promoter-2 as a promoter enables a gene of interest to be expressed specifically in the vascular bundle system regardless of the growth stage and the type of organs. This activity is useful for allowing an expression targeting the vascular bundle at an individual plant level, for example, for an expression system directed towards the improvement of the transport capacity of vascular bundles, the modification of herbaceous type, and others.

Still further, by a combined use of these promoters, it is possible to promote expression of a gene of interest in such a manner that the specificity is selected to individual fine tissues (e.g., phloem, xylem or vascular parenchymatous cells) within the vascular bundle system or to the growth stage.

The term "vascular bundle" is used herein to include: vascular bundle sheath (including vascular parenchymatous cells) which is consisted of phloem (including phloem companion cell or phloem liquid and acting as an organ for conducting assimilation products or water) and xylem; longitudinal and transverse vascular bundles running on green leaves of a rice plant such as a leaf sheath or leaf blade; and any other vascular bundles existing in organs such as glumous flower, pistil (stigma), filament, lodicule or ovary wall (pericarp) during the flowering and maturation periods (however, the gene is expressed in the entire ovary wall tissues in the initial stage of maturation and around 3 days after flowering). Moreover, the term "specific to the vascular bundle" is used to mean that gene expression is almost specific to the above described vascular bundle sheath, but a preferred promoter is specific especially for the phloem tissues in the vascular bundle. Further, the term "specific to the growth stage", is used to mean that the promoter of the invention is specific to the node and internode during the period of internode elongation, or specific to certain periods such as the periods of heading or flowering/ripening. Moreover, the term "specific to the growth stage" is sometimes used to mean that the promoter is specific to the phloem in nodes or internodes, or specific to certain organ(s) during heading or flowering period. Therefore, in one embodiment of the invention, the specificity of promoters having both site and time-specificities is also included in the definition of the term "expression specificity" in the specification.

The promoter of the present invention with the above-described features is useful, when an anti-pest protein, antiviral protein, disease resistance protein or the like is expressed so as to impart disease and insect damage resistance to plants. Moreover, the promoter of the invention is also useful, when a sugar metabolism (sucrose synthase, sucrose phosphate synthase, etc.) or a sugar transport (SUT, $H^+$-ATPase, etc.) system protein or a gene encoding a sugar signal transduction factor is expressed specifically in the vascular bundle so as to improve glucose transport environment through the vascular bundle. In addition, the present promoter is useful particularly when a protein is expressed for the purpose of transporting substances through the phloem.

EXAMPLES

Isolation of OsSUT1 Genomic Clone

Using a genomic DNA extraction kit, ISOPLANT (Nippon Gene Co., Ltd.), genomic DNA was isolated and purified from the green leaf of a rice variety (*Oryza sativa* L.), "Aoinokaze". DNA (100 μg) was partially digested with a restriction enzyme, Sau3AI (Pharmacia Corp.). The thus obtained DNA was concentrated by isopropanol precipitation, and then subjected to centrifugation on the continuous density gradient of 20 to 5% (w/v) NaCl to provide fractions each in a small volume. The DNA size of each fraction was determined by agarose gel electrophoresis. Thereafter, the DNA in fractions of a size of 23 to 15 kbp was ligated into the XhoI site of λ BlueSTAR vector (trade name; manufactured by Novagen), and then a genomic library was produced by package mix using Gigapack Gold (trade name; manufactured by Stratagene). Using, as a probe, a BamHI-EcoRI fragment (814 bp) that is a portion of an OsSUT1 cDNA sequence, the genomic library was screened by a conventional method (Sambrook, J., Fritsch, E. F. and Maniatis, T. (1989): Molecular cloning: A laboratory manual, second ed., Cold Spring Harbor Laboratory Press, Cold Spring Harbor, N.Y.). Three positive clones were obtained. Each of these clones was digested with randomly selected 5 types of restriction enzymes, and thereafter, Southern hybridization analysis was carried out using the BamHI-EcoRI fragment (814 bp) from the OsSUT1 cDNA sequence as a probe. As a result, an EcoRI fragment (4 kbp) showing the strongest signal was isolated as a fragment containing the OsSUT1 structural region. The nucleotide sequence of the obtained fragment was determined using ABI Prism™ Bigdye™ Terminator Cycle Sequencing Kit and 373A DNA Sequencer (both products manufactured by Applied Biosystems (PERKIN ELMER)). As a result, it was found that the nucleotide sequence comprised the 5'-side structural region of OsSUT1 and the 1403 bp upstream region flanking to the translation initiation site (refer to FIG. 9).

Construction of Vector to Examine OsSUT1 Promoter Activity

Synthetic primers were designed so as to comprise restriction site sequences at both ends. Using the synthetic primers and Takara EX Taq polymerase (trade name; manufactured by TaKaRa Shuzo Co., Ltd.), the promoter region of OsSUT1 was amplified by PCR. The sequences of the synthetic primers employed are as follows:

[Forward primer]
(SEQ ID NO: 2)
1. 5'-TCG<u>GCG GCC GCG</u> ATA TCG AAT TCG CTA GGC GT-3'
   (underline: NotI restriction site)

(SEQ ID NO: 3)
2. 5'-AGC<u>TCT AGA</u> GTT GGC AGG TGC ACC ACC CTT-3'
   (underline: XbaI restriction site)

[Reverse primer]
(SEQ ID NO: 4)
3. 5'-CTG<u>GGA TCC</u> GCC ATG GCG GAC GCG CCA CG-3'
   (underline: BamHI restriction site)

When the translation initiation site was set as the origin·+1, using the above primers 1 and 3, an amplified fragment of −1119 to +14 bp (1133 bp) was obtained, and using the above primers 2 and 3, another amplified fragment of −315 to +14 bp (329 bp) was obtained. Moreover, the amplified fragment of 1133bp was cleaved with a restriction enzyme XbaI to obtain a fragment of −455 to +14 bp (496 bp) containing the translation initiation site. These three fragments were cleaved with the restriction enzymes which corresponded to the linkers as shown below.

Figure 2:
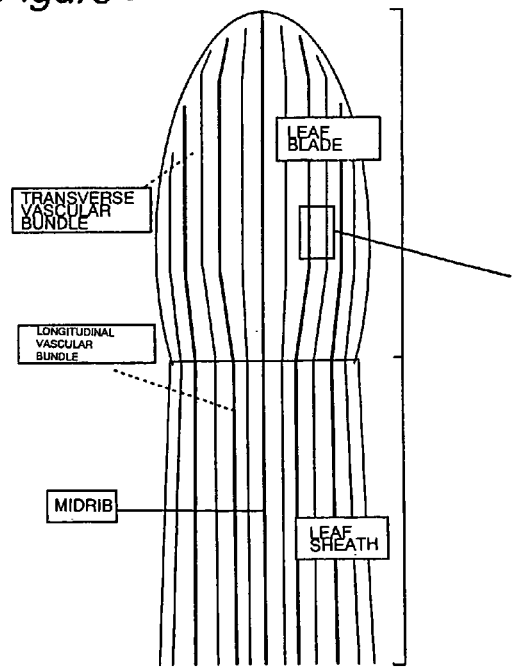
FIG. 2 shows the running state of vascular bundles on the portion from the leaf blade to the leaf sheath of a rice plant.
Figure 2:
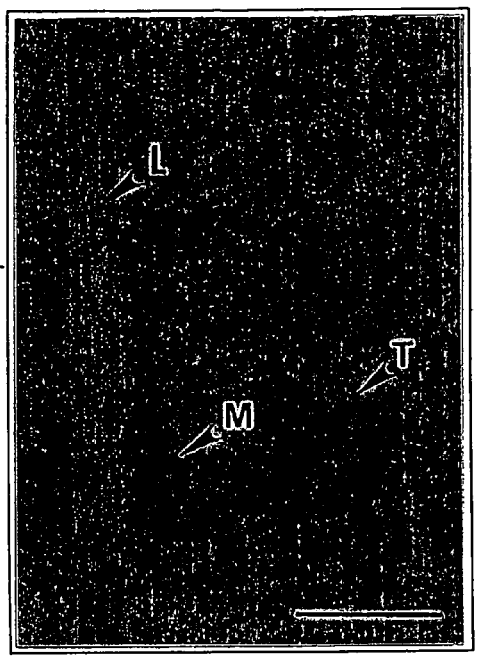
Figure 2:
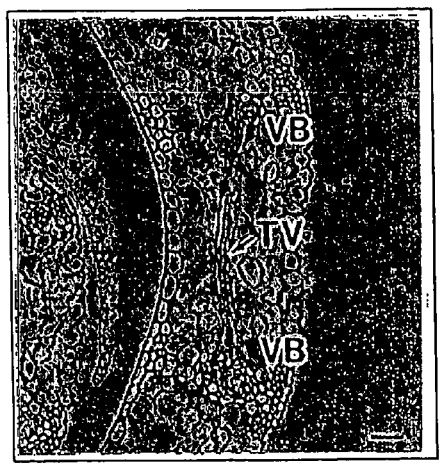

DNA fragment 1: a 1133 bp fragment: NotI and BamHI
DNA fragment 2: a 469 bp fragment: BamHI
DNA fragment 3: a 329 bp fragment: XbaI and BamHI As shown in FIG. 2, each of these three amplified fragments was inserted into the restriction enzyme site of pBSII vector, and a GUS-NOS gene fragment (derived from pBI121) cleaved with SmaI and EcoRI was further ligated downstream thereof. Subsequently, both ends of the three types of promoter sequences and the region ligated to the GUS structural region were sequenced using ABI Prism™ Bigdye™ Terminator Cycle Sequencing Kit and 373A DNA Sequencer (both products manufactured by Applied Biosystems; the present PERKIN ELMER). As a result, the sequences of the both ends matched with the above genomic sequence, and it was therefore confirmed that nucleotide sequences of interest were amplified. Moreover, no abnormality such as a frame-shift was observed at the region linking to the GUS structural region.

Each of the above DNA fragments and the above GUS structural region were incorporated into a vector, and the vector was then amplified. Thereafter, in the amplified vector, transcriptional promoter controlling regions were defined as follows. The 1108 bp upstream region flanking to the translation initiation site was defined as OsSUT1-promoter-1 (refer to FIG. 9) for the above DNA fragment 1 (1133 bp), the 456 bp upstream region flanking to the translation initiation site was defined as OsSUT1-promoter-2 (refer to FIG. 10) for the above DNA fragment 2 (469 bp), and the 306 bp upstream region flanking to the translation initiation site was defined as OsSUT1-promoter-3 (refer to FIG. 11) for the above DNA fragment 3 (329 bp).

A cassette comprising a promoter:GUS-NOS fragment was cleaved with NotI and HindIII from the respective vector comprising one of the DNA fragments 1 to 3, and thereafter it was inserted into the corresponding restriction enzyme site of an intermediate vector pSB100. The thus obtained vectors were introduced into *Escherichia coli* LE392, and then subjected to introduction into *Agrobacterium* and homologous recombination by triple cross using *Agrobacterium* LBA4404/pSB4 and *Escherichia coli* HB101/pRK2013 (Komari, T. et al., Plant J. (1996) 10: 165–174).

Production of Transformed Rice by the *Agrobacterium* Method

Using a Japonica type rice variety "Asanohikari", the *Agrobacterium* method was carried out as previously reported (Hiei, T. et al., (1994) Plant J. 6: 271–282). The obtained transformant was grown in an air-conditioned green house (lighting period: 16 hours; temperature: 28° C. (day), 23° C. (night)).

GUS Staining

After transformation, the obtained callus was cultured in an N6 medium containing hygromycin (50 g/ml) for redifferentiation for 4 or 5 weeks, and thereafter the selected plants were used as transformants in GUS staining. The redifferentiated young plants were grown until the 5- or 6-leaf stage, and the green leaves and roots were subjected to GUS staining according to the method of Kosugi, S. et al. (Plant Science (1990) 70: 133–140). The preparation of the section used to analyze tissue-specific expression was carried out according to the method of Murakami et al. (Syokubutsu Saibo Kogaku (1992) 4: 281–286), using Microslicer DTK-1000 (Dohan E M).

Analysis of Promoter Expression by Staining (Refer to FIGS. 2 to 7)

Three groups of rice plants were selected, each of which consisted of thirty rice plants where OsSUT1-promoter-1, -2 or -3 was introduced, respectively. Then, rice plants which were positively stained by GUS were subjected to the detailed observation of tissue specificity. As shown in FIG. 2, in the rice vascular bundle system tissues, large vascular bundles surrounded by small vascular bundles between a leaf blade and a leaf sheath run in the longitudinal direction, and transverse vascular bundles run so that they link to these in the transverse direction. In each photograph in the figure, symbol VB represents a longitudinal vascular bundle, symbol L represents a large vascular bundle (longitudinal) in the longitudinal vascular bundles, symbols TV and T represent transverse vascular bundles, and symbol M represents a small vascular bundle in the longitudinal vascular bundles.

Figure 3:
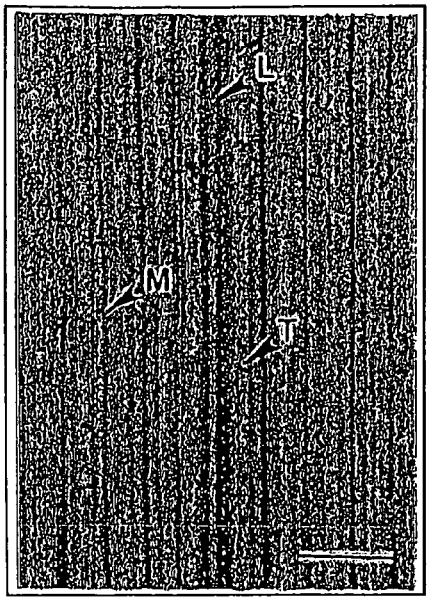
FIG. 3 is a photograph showing the activity of OsSUT1-promoter-1 by GUS staining.
Figure 3:
Figure 3:
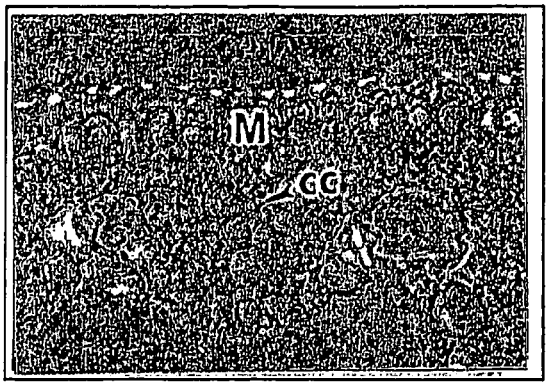
Figure 3:
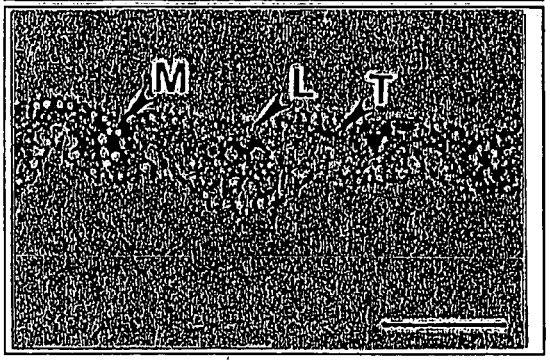
Figure 3:
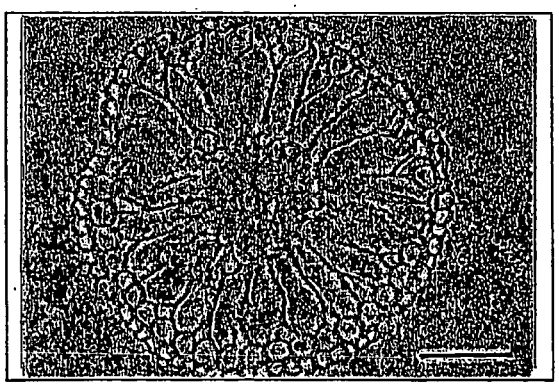
Figure 3:
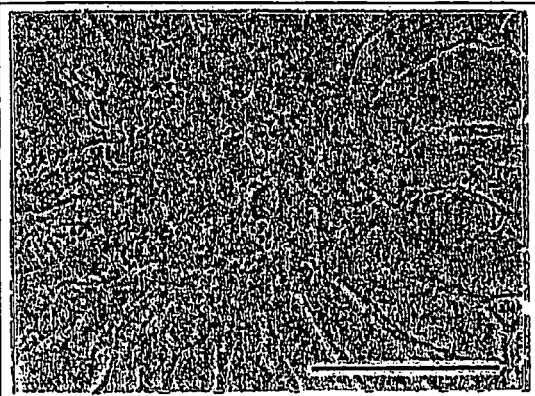

As shown in FIG. 3, in the rice plant into which OsSUT1-promoter-1 was introduced, strong expression was observed in the phloem in the vascular bundle of the green leaves. In the photograph, the phloem which is located in the center of both in the longitudinal vascular bundle M and in the transverse vascular bundle T, was selectively stained and so a very contrasting pattern was formed. This is consistent with the result of in situ analysis (Matsukura, C. et al., Plant Physiol. (2000) 124: 85–94) using the cDNA of OsSUT1 as a probe, and it is therefore considered that these results reflect the actual expression of OsSUT1.

Figure 4:
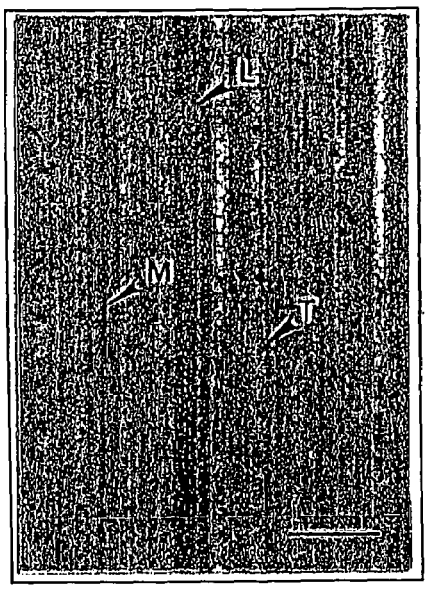
FIG. 4 is a photograph showing the activity of OsSUT1-promoter-2 by GUS staining.
Figure 4:
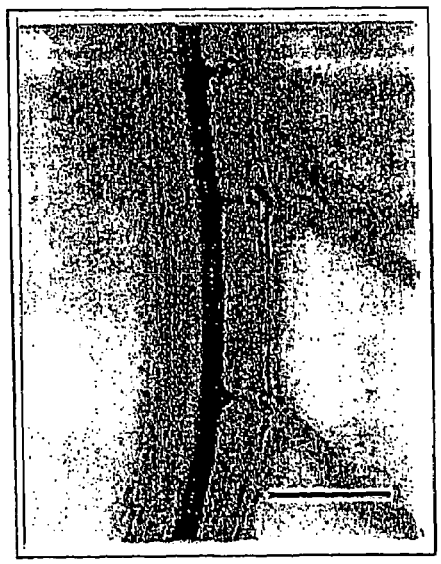
Figure 4:
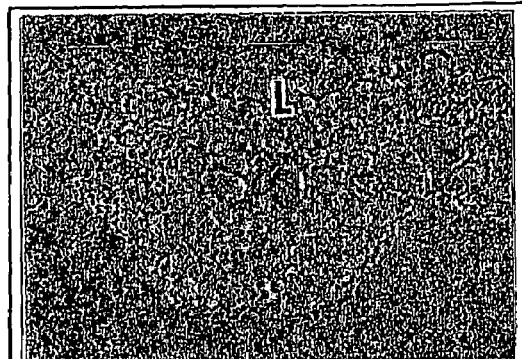
Figure 4:
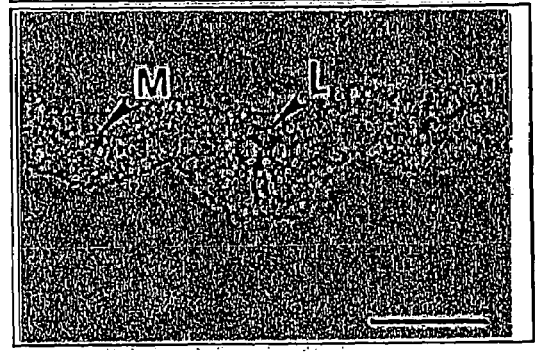
Figure 4:
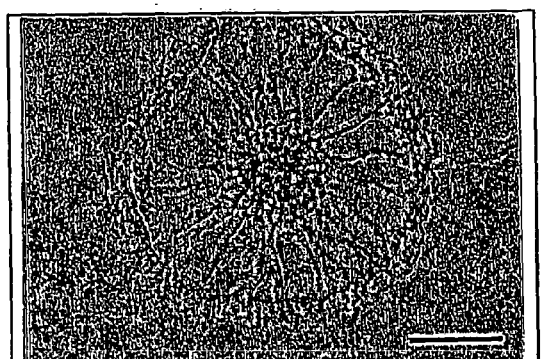
Figure 4:
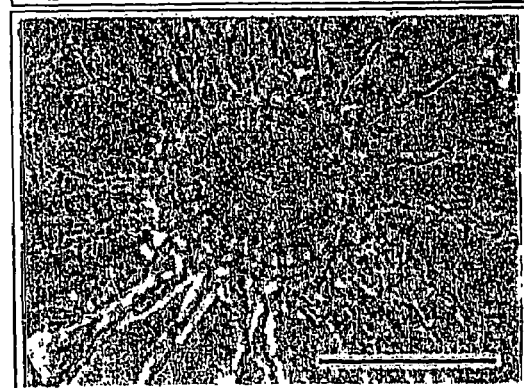

In contrast, as shown in FIG. 4, being different from the case of OsSUT1-promoter-1, the rice plant into which OsSUT1-promoter-2 was introduced did not show a clear pattern of light and dark between the phloem of each vascular bundle and the xylem surrounding it, but the whole vascular bundle sheath in general was stained. That is, it was found that plants showed gene expression in the vascular bundle sheath (the phloem, the xylem and the vascular bundle parenchymatous cells) of the green leaves and roots, but that the specificity for the phloem tended to have been lost when OsSUT1-promoter-2, having a deletion of 652 bp in the 5'-side area of OsSUT1-promoter-1, was introduced thereinto.

Figure 5:
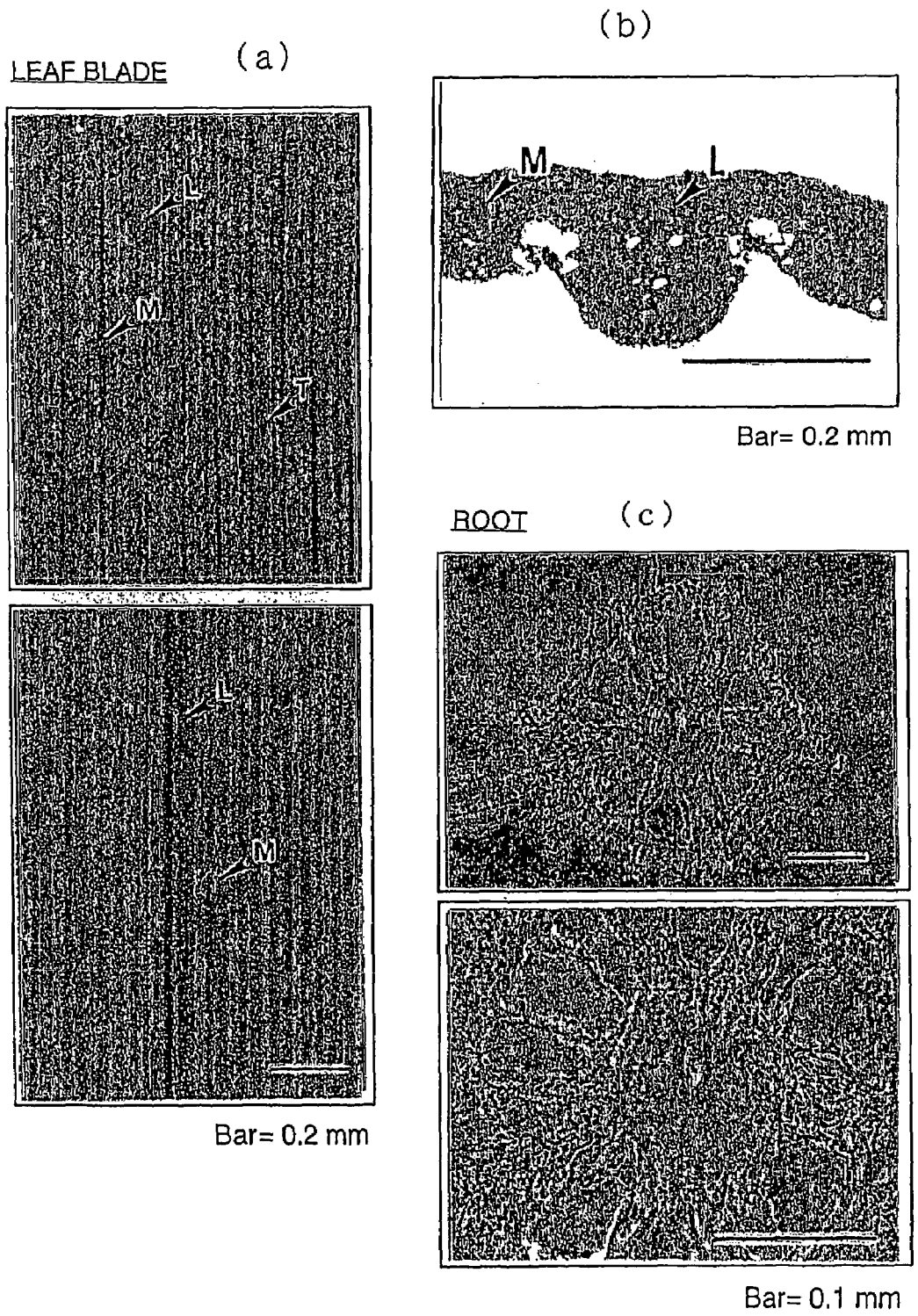
FIG. 5 is a photograph showing the activity of OsSUT1-promoter-3 by GUS staining.
Figure 6:
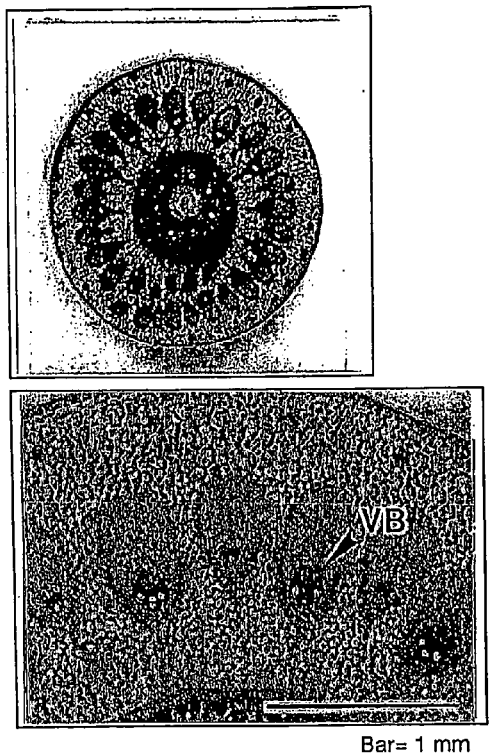
FIG. 6 shows the activity of OsSUT1-promoter-1 in the nodes and the internodes during the heading period by GUS staining.
Figure 6:
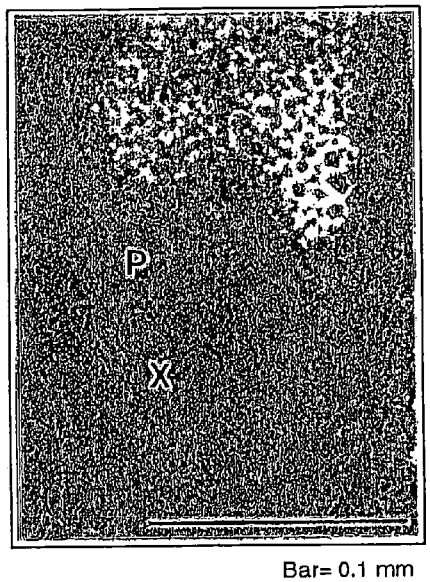
Figure 6:
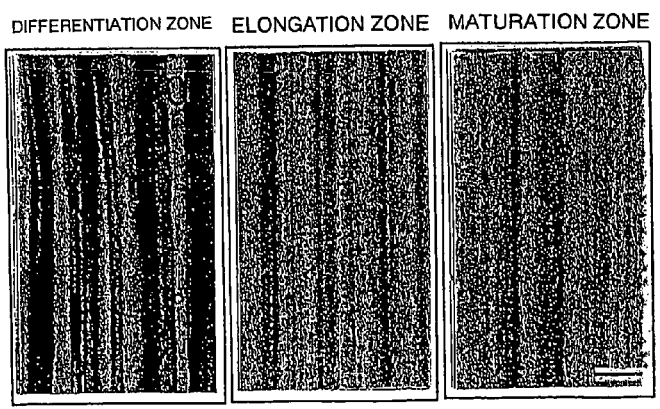
Figure 6:
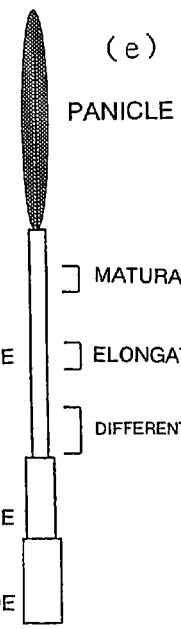

Further, with regard to plants into which OsSUT1-promoter-3, having a deletion of 802 bp in the 5'-side area of OsSUT1-promoter-1, was introduced, the number of plants which were positive by GUS staining was reduced overall, and as shown in FIG. 5, even in the positive plants, the entire leaf sheath tended to be stained, thereby showing little specificity to vascular bundles.

Figure 7:
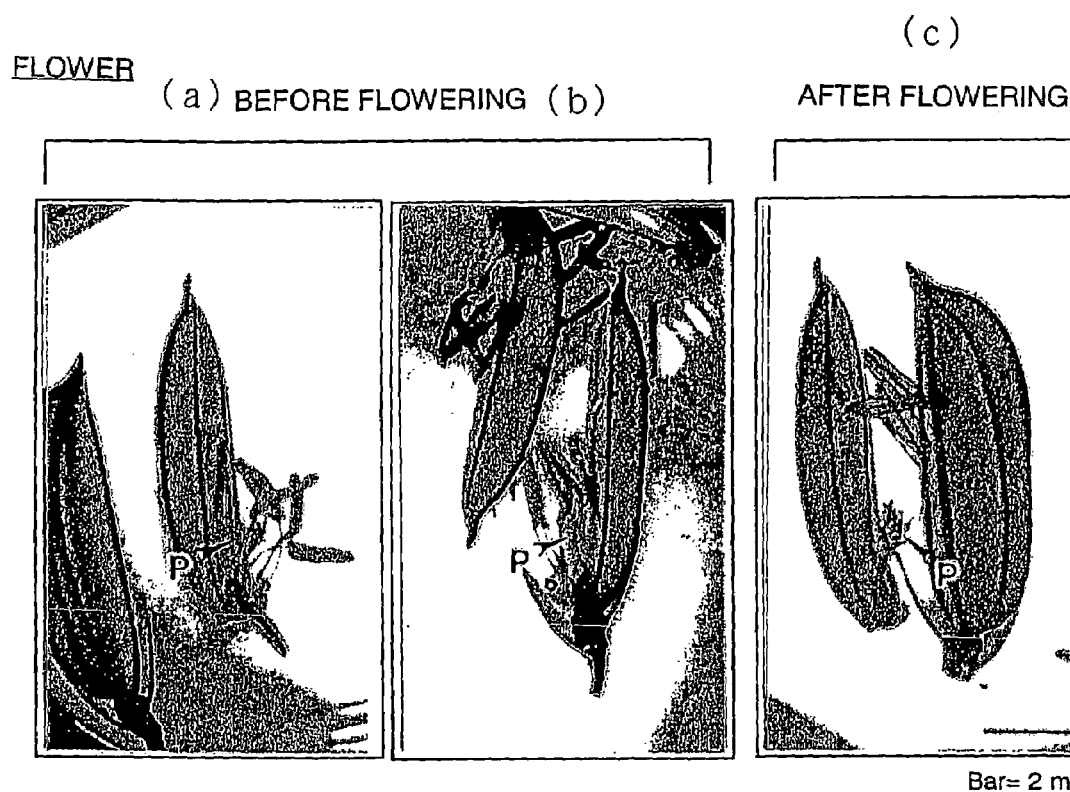
FIG. 7 shows the activity of OsSUT1-promoter-1 in a flower organ during the flowering period by GUS staining. Each of FIGS. 7a and 7b is a magnified picture of a flower organ region comprising a glumous flower before flowering. Each of FIGS. 7c and 7d is a magnified picture of a flower organ region comprising a glumous flower immediately after flowering.
Figure 7:
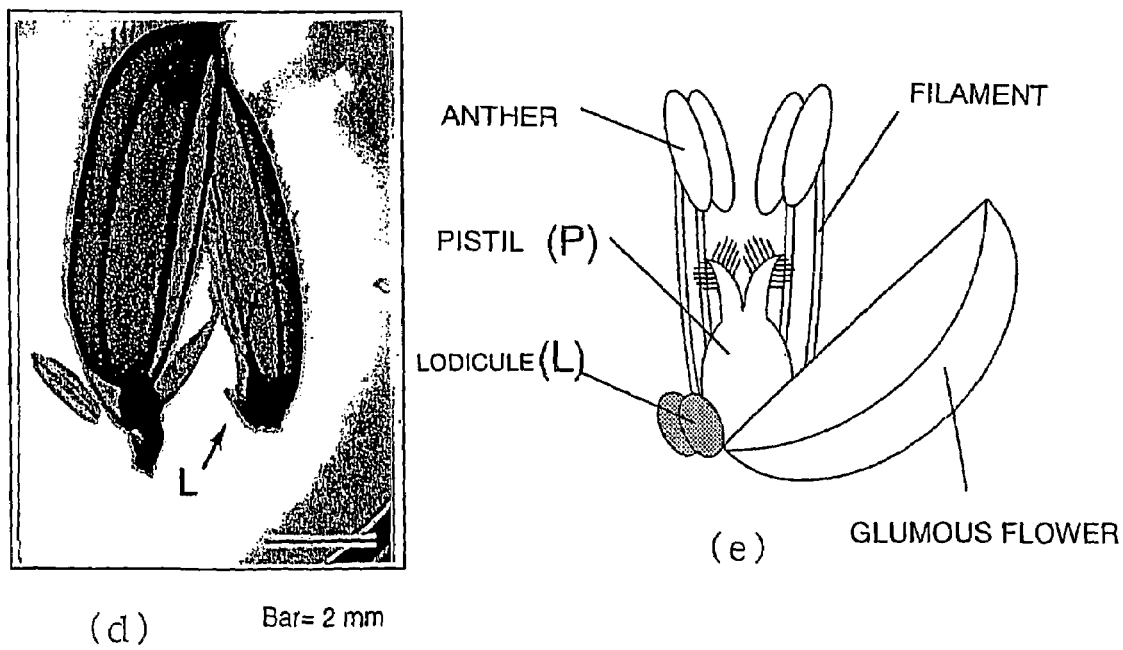
Figure 8:
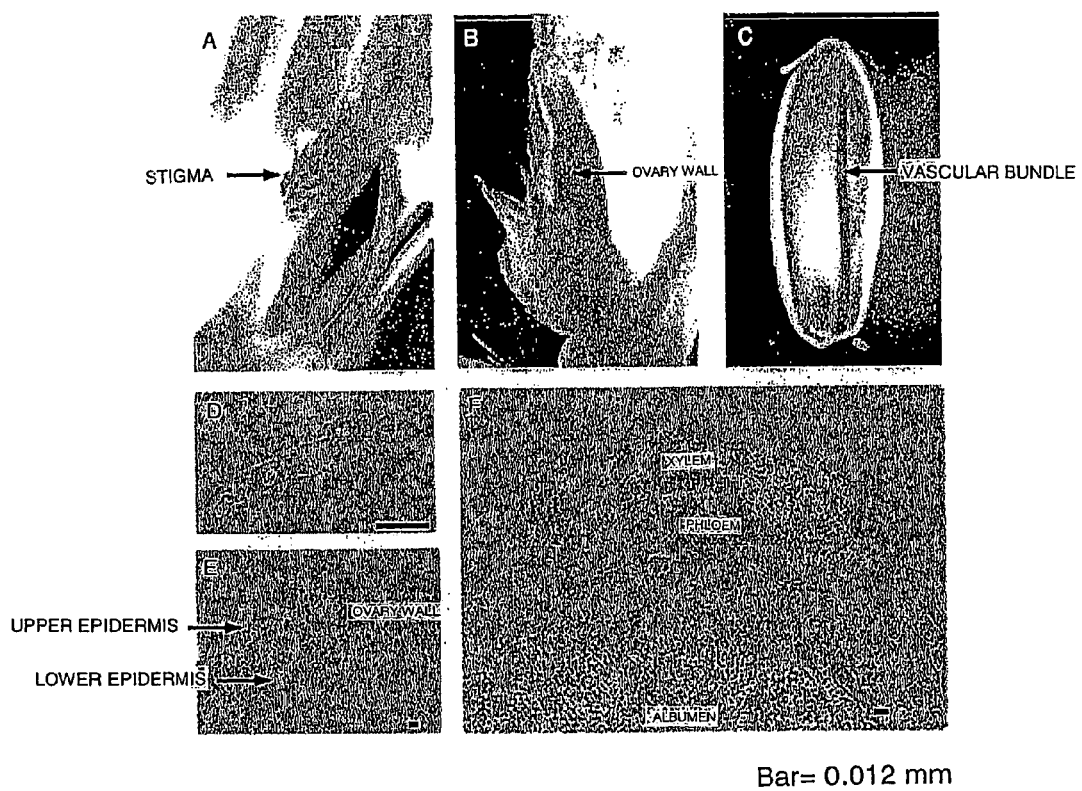
FIG. 8 is a photograph showing the activity of OsSUT1-promoter-1 in flower organ region during the flowering and ripening periods.

To analyze growth stage specificity, the plants into which OsSUT1-promoter-1 was introduced were successively grown in a pot, and the gene expression until flowering was analyzed by GUS staining. As a result, OsSUT1-promoter-1 showed strong gene expression in the phloem in the vascular bundle of the node and the internode during the internode elongation period (FIG. 6), and in the vascular bundle of the glumous flower, the pistil (stigma), the filament and the lodicule during the flowering period (since these are very small structures, it was impossible to distinguish the phloem from the xylem by this analysis) (FIGS. 7 and 8). Moreover, the gene expression was observed also in the entire ovary wall (until 3 days after flowering, especially in the upper epidermis and the lower epidermis) and the phloem in the pericarp vascular bundle (around 10 days after flowering) in the initial stage of the ripening period (FIG. 8). The results showing site specificity and time specificity as described above, is consistent with the results obtained by Northern blot analysis (Hirose, T. et al., (1997) Plant Cell Physiol. 38: 1389–1396).

From the above results, the inventors have reached the following conclusion:

(1) OsSUT1-promoter-1 (−1108 to −1) has a strong site-specific promoter activity targeting the phloem in the vascular bundle. Moreover, it has the promoter activity not only in green leaves but also in nodes, internodes and flower organs during the heading, flowering and ripening periods, in time specific manner in addition to being specific to the vascular bundle.

(2) OsSUT1-promoter-2 (−456 to −1) has a specific promoter activity which promotes expression of genes in the entire vascular bundle sheath of green leaves and roots, that is, in the phloem, the xylem, and the vascular bundle parenchymatous cells. The specificity for the vascular bundle is maintained, but the specificity for the phloem is lost by the deletion of a region from −1108 to −457. Accordingly, it is predicted that a promoter sequence relating to phloem-specific expression exists in the region of −1108 to −457. Moreover, the tendency that phloem specificity and time specificity are relaxed by the deletion of the region so that a gene is expressed in the entire vascular bundle sheath can effectively be used for the control of the overexpression or suppressed expression of gene targeting the parenchymatous cells and the xylem in the vascular bundle.

(3) Since OsSUT1-promoter-3 (−306 to −1) did not show vascular bundle specific expression, it is considered that the promoter sequence relating to the expression specificity of OsSUT1 exists in a region from −1108 to −307 bp.

Construction of Expression System Using the Above Promoter

To actually express a gene encoding a useful protein, a structural gene encoding a desired protein may be incorporated instead of the above GUS-NOS sequence. At this time also, the amplification and screening of each DNA, the construction of an expression cassette and an expression vector, transformation, regeneration and others can be carried out by techniques well known to a person skilled in the art, as described above.

The invention claimed is:

1. An isolated DNA molecule, having a specific promoter activity in a phloem in plant vascular bundle tissues and comprising a sequence having identity of 100% to the nucleic acid sequence set forth in SEQ ID NO: 1 from the guanine at position 296 to the cytosine at position 1403.

2. An isolated DNA molecule having a specific promoter activity in plant vascular bundle tissues and comprising a sequence having identity of 100% to the nucleic acid sequence set forth in SEQ ID NO:1 from the guanine at position 948 to the cytosine at position 1403.

3. An expression cassette, comprising:
    a DNA sequence having promoter activity in a phloem in plant vascular bundle tissues or having promoter activity in plant vascular bundle tissues comprising a) a nucleotide sequence having a sequence identity of 100% to the nucleic acid sequence set forth in SEQ ID NO:1 from the quanine at position 296 to the cytosine at position 1403, wherein said promoter activity is in said phloem in plant vascular bundle tissues, or b) a nucleotide sequence having a sequence identity of 100% to the nucleic acid sequence set forth in SEQ ID NO:1 from the thymine at position 948 to the cytosine at position 1403, wherein said promoter activity is in said plant vascular bundle tissues; and a foreign polynucleotide sequence, which is expressed in said phloem in plant vascular bundle tissues or in said plant vascular bundle tissues, respectively, wherein said polynucleotide sequence is ligated downstream of said DNA sequence.

4. The expression cassette of claim 3, wherein said foreign polynucleotide sequence imparts disease resistance to a plant.

5. The expression cassette of claim 3, wherein said foreign polynucleotide sequence is an anti-pest protein, an antibacterial protein or an antiviral protein.

6. The expression cassette according to claim 3, which further comprises a marker gene polynucleotide sequence for selecting a transformant.

7. A vector for transformation which comprises the expression cassette according to claim 3 or 6:
wherein said nucleotide sequence has a sequence identity of 100% to the nucleic acid sequence set forth in SEQ ID NO:1 from the thymine at position 948 to the cytosine at position 1403.

8. A transformed plant cell, a callus obtained from the cell, a transformed plant obtained from the callus, or a transgenic progeny thereof, comprising a DNA sequence having promoter activity in the phloem in plant vascular bundle tissues or in plant vascular bundle tissues, wherein said DNA sequence comprises a sequence having identity of 100% to the nucleic acid sequence set forth in SEQ ID NO:1 from the quanine at position 296 to the cytosine at position 1403, and said promoter activity is in said phloem in said vascular bundle tissues or wherein said DNA sequence comprises a sequence having identity of 100% to the nucleic acid sequence set forth in SEQ ID NO:1 from the thymine at position 948 to the cytosine at position 1403, and said promoter activity is in said plant vascular bundle tissues;

and a foreign polynucleotide sequence connected downstream of the DNA sequence incorporated therein, the foreign polynucleotide sequence being expressed specifically in the phloem in plant vascular bundle tissues or in the plant vascular bundle tissues.

9. The transformed plant cell, the callus obtained from the cell, the transgenic plant obtained from the callus, or the transgenic progeny thereof according to claim 8, which is a monocotyledon.

10. A method of producing a transgenic plant expressing a desired structural polynucleotide sequence specifically in the phloem in vascular bundle tissues or in the vascular bundle system tissues, which comprises the steps of:

(a) providing a DNA molecule according to any one of claims 1 or 2;

(b) ligating the desired structural polynucleotide sequence downstream of said DNA molecule, and ligating a selective marker polynucleotide sequence downstream of said structural polynucleotide sequence, so as to produce an expression cassette;

(c) introducing said expression cassette in to the genome of a plant by *Agrobacterium* method, electroporation, PEG method, microinjection or particle gun method;

(d) obtaining a transformed plant cell and subjecting the obtained cells to callus culture; and (e) culturing the generated callus in a regeneration medium until it becomes a complete plant.

11. The expression cassette of claim 3, which comprises the nucleotide sequence having a sequence identity of 100% to the nucleic acid sequence set forth in SEQ ID NO:1 from the quanine at position 296 to the cytosine at position 1403.

12. The expression cassette of claim 3, which comprises the nucleotide sequence having a sequence identity of 100% to the nucleic acid sequence set forth in SEQ ID NO:1 from the thymine at position 948 to the cytosine at position 1403.

13. The transformed plant cell, the callus derived from the cell, the transgenic plant obtained from the callus, or the transgenic progeny thereof according to claim 8, which is a monocotyledon, which comprises the nucleotide sequence having a sequence identity of 100% to the nucleic acid sequence set forth in SEQ ID NO:1 from the guanine at position 296 to the cytosine at position 1403.

14. The transformed plant cell, the callus obtained from the cell, the transgenic plant obtained from the callus, or the transgenic progeny thereof according to claim 8, which is a monocotyledon, which comprises the nucleotide sequence having a sequence identity of 100% to the nucleic acid sequence set forth in SEQ ID NO:1 from the thymine at position 948 to the cytosine at position 1403.

* * * * *